United States Patent
Kurita et al.

(10) Patent No.: US 6,897,184 B2
(45) Date of Patent: May 24, 2005

(54) ENHANCER FOR AGRICULTURAL CHEMICALS

(75) Inventors: Kazuhiko Kurita, Wakayama (JP); Tadayuki Suzuki, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 10/448,204

(22) Filed: May 30, 2003

(65) Prior Publication Data

US 2004/0038826 A1 Feb. 26, 2004

(30) Foreign Application Priority Data

May 31, 2002 (JP) .......................................... 2002-159918

(51) Int. Cl.$^7$ .......................... A01N 25/30; A01N 57/02
(52) U.S. Cl. ...................... 504/116.1; 504/206; 424/405
(58) Field of Search ............................. 504/116.1, 206; 424/405

(56) References Cited

U.S. PATENT DOCUMENTS 5,750,468 A * 5/1998 Wright et al. ................ 504/206

FOREIGN PATENT DOCUMENTS

| JP | 1-268605 A | 10/1989 |
|---|---|---|
| JP | 01268605 | 10/1989 |
| JP | 1-299205 A | 12/1989 |
| WO | WO 95/17817 A1 | 7/1995 |
| WO | WO 95/31903 A1 | 11/1995 |
| WO | WO97/01423 A1 | 1/1997 |
| WO | WO01/08482 A1 | 2/2001 |
| WO | WO02/069718 A2 | 9/2002 |
| WO | WO02/096199 A2 | 12/2002 |

* cited by examiner

*Primary Examiner*—S. Mark Clardy
(74) *Attorney, Agent, or Firm*—Birch, Stewart, Kolasch & Birch, LLP

(57) ABSTRACT

This invention provides an agricultural chemical composition comprising an enhancer for agricultural chemicals, which is excellent in stability even when compounded at high concentration, and exerts an excellent effect-enhancing action on agricultural chemicals. A specific amine oxide having a $C_{6-30}$ alkyl or alkenyl group or an alkylphenyl group having a $C_{6-17}$ alkyl group, and an amide alkyl group or oxyalkylene group is used as the enhancer for agricultural chemicals.

14 Claims, No Drawings

ENHANCER FOR AGRICULTURAL CHEMICALS

TECHNICAL FIELD

The present invention relates to an agricultural chemical composition comprising an enhancer for agricultural chemicals.

BACKGROUND ART

Agricultural chemicals including an insecticide, a fungicide or a bactericide, a herbicide, a miticide and a plant growth regulator, are used in the form of emulsifiable concentrates, wettable powders, granules, dust formulations, suspension concentrates or flowables, liquid formulations etc. For sufficiently deriving the effect of a technical material of agricultural chemical, an agricultural chemical with improvements in the physical properties thereof is extensively devised, but further enhancement of the effect of the agricultural chemical is difficult at present by devising the formulation. Development of novel agricultural chemicals is more difficult, and therefore, further enhancement of the activity of existing agricultural chemicals is significantly meaningful in industry.

It is known that various surfactants have been utilized as an enhancer for agricultural chemicals. For example, it is known that a composition exerting a strong effect on bipyridinium herbicide can be obtained by combining an anionic surfactant with a chelating agent (WO95/31903). Further, it is also known that a highly effective effect-enhancing composition for agricultural chemicals can be obtained by compounding a chelating agent with a cationic surfactant and adding another surfactant thereto (WO95/17817).

Further, an alkyl or alkenyl polyoxyalkylene ether acetate is known to have a strong effect, but when used in combination with various additives such as a chelating agent, a thickener, or inorganic materials, is poor in stability which makes manufacturing of a formulation very difficult, and is thus not practically used often. The stability thereof gets worse particularly when blended at a high concentration. Further, the alkyl or alkenyl polyoxyalkylene ether acetate is highly acidic (pH 2 or thereabout), and is thus not only may be dangerous when used, but also may, when used in a formulation, decompose other surfactants and technical materials of agricultural chemicals, which lowers their activity. Further, the use of an amine oxide as an enhancer for agricultural chemicals is also known (JP-A 1-268605), but there is a demand for further improvements in the effect-enhancing action.

In JP-A 1-299205, the storage stability of Vasta (glyphosinate) is improved by the use of a surfactant.

SUMMARY OF THE INVENTION

The present inventors found that a specific alkyl or alkenyl amine oxide has a stronger effect-enhancing action on various agricultural chemicals, to complete the present invention.

That is, the present invention provides an enhancer for agricultural chemicals, which comprises a compound represented by formula (I) below.

The present invention relates to an agricultural chemical composition comprising the following components (A) and (B):

(A)

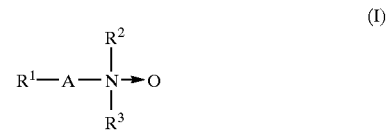

wherein $R^1$ represents a $C_{6-30}$ linear or branched alkyl group, a $C_{6-30}$ linear or branched alkenyl group, or an alkylphenyl group having a $C_{6-17}$ alkyl group; $R^2$ and $R^3$ each represents a $C_{1-30}$ linear or branched alkyl group, a $C_{1-30}$ linear or branched alkenyl group, or $-(A^1O)_m-H$; A represents $-CONH(CH_2)_n-$ or $-(OA^1)_m-$; $A^1$ represents a $C_{2-4}$ alkylene group, the average of m is a number of 1 to 30, and the average of n is a number of 1 to 15, and (B) a technical material of agricultural chemicals selected from the group consisting of a herbicide selected from glyphosate and bialaphos, an insecticide, a fungicide or a bactericide and a miticide.

The composition of the present invention may further comprise a surfactant (C) other than (A). The composition may further comprise a chelating agent (D).

The (A)/(C) ratio is preferably in the range of 1/10 to 50/1 by weight. The molar ratio of (D) to (A) is preferably in the range of 0.05/1 to 15/1.

The present invention also provides the use of (A) described above as an enhancer for (B) described above, and a method of enhancing the effect of (B) by applying (A) described above to (B) described above.

DETAILED DESCRIPTION OF THE INVENTION

When used in combination with a technical material of agricultural chemical, the enhancer for agricultural chemicals which comprises the compound (A) of the general formula (I) according to the present invention may improve the effect of the technical material of agricultural chemical, preferably two or three times as much as otherwise.

Although not wanting to be limited by theory, although the mechanism for the enhancer for agricultural chemicals comprising the compound (A) of the general formula (I) as the active ingredient in the present invention which exhibits a significant effect-enhancing action regardless of the type of agricultural chemical structure is not completely known, it is estimated that when added to an agricultural chemical, the enhancer of the present invention promotes penetration of the agricultural chemical, into plants, insects, fungi or bacteria.

<Compound (A)>

In the general formula (I) of compound (A), $R^1$ is preferably a group selected from a $C_{8-24}$ linear or branched alkyl group, a $C_{8-24}$ linear or branched alkenyl group, and an alkylphenyl group having a $C_{6-17}$ alkyl group. In the general formula (I), each of $R^2$ and $R^3$ is preferably a group selected from a $C_{1-18}$ linear or branched alkyl group, a $C_{1-18}$ linear or branched alkenyl group and $-(A^1O)_m-H$. In the general formula (I), A is preferably $-CONH(CH_2)_n-$ wherein the average of n is a number of 1 to 3, or $-(OA^1)_m-$ wherein the average of m is a number of 1 to 15, among which $-CONH(CH_2)_n-$ wherein the average of n is a number of 1 to 3 is preferable. These are preferable from the viewpoint of the effect-enhancing action on agricultural chemicals.

One example of a process for producing the compound (A) is as follows: A fatty acid and dimethylaminopropylamine, which are the starting materials of the desired compound (A), are reacted at a high temperature and purified, to synthesize an amide amine as an intermediate. Thereafter, the amide amine is reacted with hydrogen peroxide in an aqueous solution to which citric acid was added, whereby the desired alkylamide propyl dimethylamine oxide as the active ingredient is produced.

The content of the compound (A) as the enhancer for agricultural chemicals according to the present invention is preferably 0.1 to 90% by weight, more preferably 1 to 50% by weight.

<Surfactant (C)>

In a preferred embodiment, by further using a surfactant (C) in combination with the compound (A), the amount of the compound (A) used as the enhancer for the agricultural chemicals according to the present invention can be reduced while maintaining the effect-enhancing action of the compound (A) on the agricultural chemicals. The surfactant (C) that can be used includes a nonionic surfactant, an anionic surfactant, a cationic surfactant and an amphoteric surfactant or a mixture thereof.

The nonionic surfactant includes polyoxyalkylene alkyl ethers such as polyoxyethylene alkyl ether (for example, polyoxyethylene oleyl ether), polyoxyalkylene alkyl aryl ethers such as polyoxyethylene alkyl phenol, a polyoxyalkylene alkyl aryl ether/formaldehyde condensate, polyoxyalkylene aryl ether, polyoxyalkylene alkyl ester, polyoxyalkylene alkyl sorbitol ester, polyoxyalkylene sorbitan ester, polyoxyalkylene alkyl glycerol ester, polyoxyalkylene block copolymers (for example, those containing a polyoxypropylene group), polyoxyalkylene block copolymer alkyl glycerol ester, polyoxyalkylene alkyl sulfonamide, polyoxyalkylene rosin ester, alkyl glycoside, alkyl polyglycoside, polyoxyalkylene alkyl polyglycoside, etc., and mixtures of two or more thereof.

Examples of the cationic surfactant include monoalkyl di-lower alkylamine, dialkyl mono-lower alkylamine, an alkylamine ethylene oxide adduct, an alkylamine propylene oxide adduct, for example, a tallow amine ethylene oxide adduct, an oleyl amine ethylene oxide adduct, a soy amine ethylene oxide adduct, a coco amine ethylene oxide adduct, a synthetic alkylamine ethylene oxide adduct, an octyl amine ethylene oxide adduct, etc. and quaternary derivatives thereof (for example, those quaternarized with methyl chloride, dimethylsulfuric acid, diethylsulfuric acid, benzyl chloride, etc.), and mixtures thereof.

Typical anionic surfactants are available as an aqueous solution or in a solid state, and examples thereof include sodium mono- and di-alkyl naphthalenesulfonate, sodium α-olefinsulfonate, sodiumalkanesulfonate, alkylsulfosuccinate, alkylsulfate, polyoxyalkylene alkyl ether sulfate, polyoxyalkylene alkyl aryl ether sulfate, polyoxyalkylene styryl phenyl ether sulfate, mono- and di-alkylbenzene sulfonate, alkyl naphthalene sulfonate, alkyl naphthalene sulfonate-formaldehyde condensates, alkyldiphenyl ether sulfonate, olefinic sulfonate, mono- and dialkylphosphate, poloxyalkylene mono- and dialkyl phosphate, polyoxyalkylene mono- and diphenyl ether phosphate, polyoxyalkylene mono- and diphenyl phenyl ether phosphate, polycarboxylate, linear and branched alkylamide polyoxyalkylene ether carboxylic acid or salts thereof, alkyl polyoxyalkylene carboxylates other than those of this invention, alkenyl polyoxyalkylene ether carboxylates other than those of this invention, aliphatic acids or salts thereof, for example, capric acid and salts thereof, lauric acid and salts thereof, stearic acid and salts thereof, oleic acid and salts thereof, N-methyl fatty acid taurides, and a mixture of two or more thereof (including salts thereof such as sodium, potassium, ammonium and amine salts)

Examples of suitable amphoteric surfactants include Armox C/12, Monaterics, Miranols, betaine, Lonzaines, and a mixture thereof.

Particularly preferable among these amphoteric surfactants are nonionic surfactants, more preferably polyoxyalkylene alkyl ethers (particularly polyoxyethylene alkyl ether) and polyoxyalkylene sorbitan esters (particularly polyoxyethylene sorbitan ester).

In a preferred agricultural chemical composition comprising the compound (A) and the surfactant (C) other than the compound (A), the compound (A)/the surfactant (C) other than the compound (A) ratio by weight, that is, (A)/(C), is preferably 1/10 to 50/1, more preferably 1/5 to 10/1.

<Chelating Agent (D)>

A chelating agent (D) may preferably be used in combination with the enhancer, e.g. the compound(A), in the agricultural chemical composition according to the present invention. The chelating agent is not particularly limited insofar as it has an ability to chelate metal ions. Examples of the chelating agent preferably used in the present invention include an aminopolycarboxylic acid-based chelating agent, an aromatic and aliphatic carboxylic acid-based chelating agent, an amino acid-based chelating agent, an ether polycarboxylic acid-based chelating agent, phosphonic acid-based chelating agents such as iminodimethyl phosphonic acid (IDP), and alkyldiphosphonic acid (ADPA), a hydroxycarboxylic acid-based chelating agent, a phosphoric acid-based chelating agent, a polymeric electrolyte (including an oligomer electrolyte) based chelating agent, and dimethyl glyoxime (DG). These chelating agents may be in the form of a free acid or in the form of a salt such as a sodium salt, potassium salt, or ammonium salt. Alternatively, they can be hydrolysable ester derivatives thereof. The molar ratio of the chelating agent (D) to the compound (A), represented by the general formula (I) as the enhancer for the agricultural chemicals is in the range of 0.05 to 15.

Examples of the aminopolycarbonic acid-based chelating agent include:
a) a compound represented by the chemical formula $RNY_2$,
b) a compound represented by the chemical formula $NY_3$,
c) a compound represented by the chemical formula R—NY—$CH_2CH_2$—NY—R,
d) a compound represented by the chemical formula R—NY—$CH_2CH_2$—$NY_2$,
e) a compound represented by the chemical formula $Y_2$N—R'—$NY_2$, and
f) a compound analogous to the compound e) and containing 4 or more Y groups, for example, a compound represented by the formula:

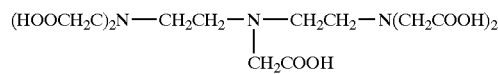

In the above formula, Y represents —$CH_2COOH$ or —$CH_2CH_2COOH$, R represents groups constituting a known chelating agent, such as a hydrogen atom, alkyl group, hydroxyl group and hydroxyalkyl group, and R' represents groups constituting a known chelating agent, such as an alkylene group and cycloalkylene group.

Typical examples of the aminopolycarboxylic acid-based chelating agent include ethylenediaminetetraacetic acid (EDTA), cyclohexanediaminetetraacetic acid (CDTA), nitrilotriacetic acid (NTA), iminodiacetic acid (IDA), N-(2-hydroxyethyl)iminodiacetic acid (HIMDA), diethylenetriaminepentaacetic acid (DTPA), N-(2-hydroxyethyl)

ethylenediaminetriacetic acid (EDTA-OH) and glycol ether diaminetetraacetic acid (GEDTA), as well as salts thereof.

Examples of the aromatic and aliphatic carboxylic acid-based chelating agents which may be used in the present invention include oxalic acid, malonic acid, succinic acid, glutaric acid, adipic acid, itaconic acid, aconitic acid, pyruvic acid, salicylic acid, acetylsalicylic acid, hydroxybenzoic acid, aminobenzoic acid (including anthranilic acid), phthalic acid, trimellitic acid and gallic acid, as well as salts, methyl esters and ethyl esters thereof. Examples of the amino acid-based chelating agents used in the present invention include glycine, serine, alanine, lysine, cystine, cysteine, ethionine, tyrosine, methionine, and salts and derivatives thereof.

Examples of the ether polycarboxylic acid-based chelating agent used in the present invention include diglycolic acid, a compound represented by the following formula, analogues compounds thereof and salts thereof (for example, sodium salts).

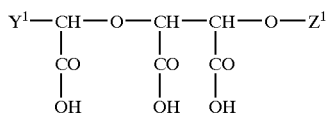

wherein $Y^1$ represents a hydrogen atom, $-CH_2COOH$ or $-COOH$, and $Z^1$ represents a hydrogen atom, $-CH_2COOH$ or

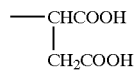

Examples of the hydroxycarboxylic acid-based chelating agent used in the present invention include malic acid, citric acid, glycolic acid, gluconic acid, heptonic acid, tartaric acid, lactic acid and salts thereof.

Examples of the phosphoric acid-based chelating agent used in the present invention include orthophosphoric acid, pyrophosphoric acid, triphosphoric acid and polyphosphoric acid.

Examples of the polymeric electrolyte (including an oligomer electrolyte) based chelating agents which may be used in the present invention include an acrylate polymer, a maleic anhydride polymer, an α-hydroxyacrylate polymer, an itaconate polymer, and a copolymer consisting of two or more monomers constituting these polymers, and an epoxysuccinate polymer.

Further, ascorbic acid, thioglycolic acid, phytic acid, glyoxylic acid and glyoxalic acid, as well as salts thereof, can also be used preferably as the chelating agent in the present invention. A pH adjusting agent, inorganic salts, a thickener, etc. can also be added if necessary to the agricultural chemical composition according to the present invention.

<Agricultural Chemical Composition>

The agricultural chemical composition of the present invention comprises an enhancer for agricultural chemicals described above and a technical material of agricultural chemical. The technical material of agricultural chemical refers to an agricultural chemical active ingredient. From the viewpoint of sufficiently achieving the effect-enhancing action on intended agricultural chemicals, it is preferable that in the agricultural chemical composition of the present invention, the ratio by weight of the compound (A) of the general formula (I) as the enhancer for the agricultural chemicals to the technical material of agricultural chemical, that is, the compound (A)/the technical material of agricultural chemical, is preferably from 0.03/1 to 50/1, more preferably from 0.04/1 to 20/1, more preferably from 0.1/1 to 10/1.

The technical material of agricultural chemical used in the agricultural chemical composition of the present invention includes those described in for example, the Agricultural Chemical Handbook, 10th ed. (in Japanese), Dec. 15, 1998, published by the Japan Plant Protection Association. Examples include, but are not limited to, the following technical material of agricultural chemicals:

The fungicides or bactericides include organic sulfur fungicides or bactericides such as zineb agent, maneb agent, thiram agent, mancozeb agent, polycarbamate agent, propineb agent etc., benzimidazole fungicides or bactericides such as benomyl agent, thiophanate-methyl agent etc., dicarboxylic acid fungicides or bactericides such as iprodione agent, procymidone agent etc., other synthetic fungicides or bactericides such as triazine agent, iminoctadine triacetate agent, isoprothiolane agent, TPN agent, probenazole agent, captan agent, fluoromide agent, DPC agent, and iminoctadine albesilate agent, sterol biosynthesis inhibitors such as triflumizole agent, bitertanol agent, pyrifenox agent, fenarimol agent, triforine agent, triadimefon agent, myclobutanil agent, difenoconazole agent, and imibenconazole agent, acid amide fungicides or bactericides such as metalaxyl agent, and mepronil agent, copper fungicides or bactericides such as inorganic copper agent, and organic copper agent, antibiotic fungicides or bactericides such as streptomycin agent, polyoxin agent, blasticidin S agent, kasugamycin agent, validamycin agent, and oxytetracycline agent, soil fungicides or bactericides such as etridiazole agent, and hymexazol agent, melamine biosynthesis inhibitors such as fthalide agent, carpropamid agent, organic phosphorus fungicides or bactericides such as IBP agent, EDDP agent, and fosetyl agent, inorganic insecticides such as inorganic sulfur agent, and hydrogen carbonate agent, methoxyacrylate fungicides or bactericides such as azoxystrobin, and kresoxim-methyl agent, anilinopyrimidine fungicides or bactericides such as mepanipyrim agent, synthetic antibiotics such as oxolinic acid agent, naturally occurring fungicides or bactericides such as soybean lecithin, and bactericides derived from living things such as antagonistic bactericides.

The insecticides include pyrethroid insecticides such as fenvalerate agent, cyfluthrin agent, permethrin agent, and flucythrinate, ethofenprox agent, organic phosphorus insecticides such as DDVP agent, MEP agent, malathion agent, dimethoate agent, PAP agent, MPP agent, DMTP agent, and EPN agent, carbamate insecticides such as BPMC agent, and NAC agent, methomyl agent, nelaistoxin insecticides such as cartap agent etc., naturally occurring insecticides such as Dalmatian pyrethrum-derived pyrethrine agent, piperonyl butoxide agent etc., rotenone agent derived from a leguminous brush Derris, sulfate nicotine agent, soybean lecithin agent, and starch agent. The insect growth regulator (IGR) includes diflubenzuron agent, teflubenzuron agent, chlorfluazuron agent, buprofezin agent, isoprothiolane agent, and flufenoxuron agent.

The miticides include a kelthane agent, BPPS agent, fenbutatinoxide agent, hexythiazox agent, amitraz agent, fenpyroximate agent, tebufenpyrad agent, halfenprox agent, and bialaphos agent, chloronicotinyl insecticides such as imidacloprid agent, other synthetic insecticides such as sodium oleate agent, and potassium oleate agent, nematocides such as D-D agent, dazomet agent, and benomyl agent, and insecticides derived from living things such as BT agent.

The herbicides include acid amide herbicides such as DCPA agent, alachlor agent, and asulam agent, urea herbicides such as DCMU agent, linuron agent etc. The bipyridinium herbicides include, for example, a paraquat agent, and diquat agent. The diazine herbicides include, for example, a bromacil agent, and lenacil agent. The S-triazine herbicides include, for example, a CAT agent, and simetryn agent. Other organic herbicides include, for example, nitrile herbicides such as DBN agent, sethoxydim agent, and crethodim agent. The dinitroaniline herbicides include, for example, trifluralin agent, and pendimethalin agent. The carbamate herbicides include a thiobencarb agent etc. The aromatic carboxylic acid herbicides include, for example, an MDBA agent etc. The phenoxy acid herbicides include a 2,4-PA agent, sihalofop-butyl agent etc. The organic phosphorus herbicides include a piperophos agent, and butamifos agent. The amino acid herbicides include glyphosate such as ammonium N-(phosphonomethyl)glycinate being available as Glyphosate, isopropylammonium N-(phosphonomethyl) glycinate being available as Roundup, trimethylsulfonium-N-(phosphonomehyl)glycinate being available in the name of Touchdown and sodium N-(phosphonomethyl)glycinate being available as Impulse, bialaphos such as L-2-amino-4-[(hydroxy)(methyl)phosphinoyl]-butyryl-L-alanyl-L-alanine being available as Herbiace. The fatty acid herbicides include a pelargonic acid agent, and DPA agent. The sulfonyl urea herbicides include a thifensulfuron-methyl agent, flazasulfuron agent, and bensulfuron-methyl agent. The pyrimidyloxybenzoic acid herbicides include bispyribac sodium salt etc. The diazole herbicides include a pyrazolynate agent etc.

Among these herbicides, the acid amide herbicides, diazine herbicides, nitrile herbicides, dinitroaniline herbicides, aromatic carboxylic acid herbicides and amino acid herbicides are preferable, and in particular the amino acid herbicides, especially a bialaphos agent or glyphosate agent, are preferable.

Further, the plant growth regulators include auxin antagonists such as maleic hydrazide agent, and uniconazole agent, auxin agents such as indolebytyric acid agent, 1-naphthaleneacetamide agent, and 4-CPA agent, cytokinine agents such as forchlorfenuron agent etc., gibberelline agents such as gibberellic acid agent, other dwarfing agents such as daminozide agent, transpiration regulators such as paraffin agent, other plant growth regulators such as choline agent, plant growth regulators derived from living things such as cholera extract, and ethylene agents such as ethephon agent.

Further, at least one component selected from a plant growth regulator, a fertilizer, a preservative, etc. other than those described above can also be used by mixing it with the agricultural chemical composition of the present invention.

The formulation of the agricultural chemical composition of the present invention may be any of an emulsifiable concentrate, a wettable powder, granule, a dust formulation, a suspension concentrate or plowable, a liquid formulation, etc., and the formulation is not limited. Accordingly, other additives such as an emulsifier, a dispersing agent, and a carrier may be optionally contained depending on the formulation. A method of using the enhancer for the agricultural chemicals according to the present invention includes a method of using the agricultural chemical composition in each formulation containing the enhancer for agricultural chemicals and a method of using the enhancer for agricultural chemicals by adding it to agricultural chemicals (not containing the enhancer of the present invention) at the time of dilution just before the use, and either method can achieve the desired effect-enhancing action of the present invention.

The surfactant (C) and the chelating agent (D) described above may also be added if necessary to the formulation of the agricultural chemical composition of the present invention. Further, a pH adjusting agent, inorganic salts and a thickener may also be added to the formulation of the agricultural chemical composition.

The pH adjusting agent which can be used in the present invention includes citric acid, phosphoric acid (pyrophosphoric acid), gluconic acid or salts thereof.

The inorganic salts which can be used in the present invention include inorganic mineral salts such as inorganic salt clay, talc, bentonite, zeolite, calcium carbonate, diatomaceous earth, and white carbon, and the inorganic ammonium salts include, for example, ammonium sulfate, ammonium nitrate, ammonium phosphate, ammonium thiocyanate, ammonium chloride, and ammonium sulfaminate.

The thickener which can be used in the present invention may be any of natural, semi-synthetic or synthetic water-soluble thickeners. Natural viscous materials include for example microorganism-derived xanthane gum or zanflow and plant-derived pectin, Arabia gum or guar gum. Semi-synthetic viscous materials include for example methylated, carboxyalkylated or hydroxyalkylated products of cellulose or starch derivatives, such as methyl cellulose, carboxymethyl cellulose or hydroxymethyl cellulose, sorbitol, etc. Synthetic viscous materials include for example polyacrylic salts, polymaleic salts, polyvinyl pyrrolidone, ethylene oxide adducts to pentaerythritol, etc.

In the present invention, a preferred use of the agricultural chemical composition comprising the enhancer for agricultural chemicals according to the present invention wherein the enhancer for agricultural chemicals is preferably contained in 0.03 to 50 times, more preferably 0.04 to 20 times, even more preferably 0.1 to 10 times as much an amount by weight as the technical material of agricultural chemical, for the purpose of killing fungi or bacteria, insects, mites or weeds or for the regulation of plant growth.

The agricultural chemical formulation using the enhancer for agricultural chemicals according to the present invention includes:

(i) an agricultural chemical formulation comprising at least one kind of compound (A) represented by the general formula (I) and an agricultural chemical composition formed as a separate package;

(ii) an agricultural chemical formulation comprising a separate package of a composition comprising at least one kind of compound (A) represented by the general formula (I) and a surfactant (C) other than the compound (A), and an agricultural chemical composition formed as a separate package;

(iii) an agricultural chemical formulation comprising a separate package of at least one kind of compound (A) represented by the general formula (I), a separate package of at least one kind of a surfactant (C) other than the compound (A), and an agricultural chemical composition formed as a separate package;

(iv) an agricultural chemical formulation comprising a separate package of a composition consisting of at least one kind of compound (A) represented by the general formula (I) and a chelating agent (D), and an agricultural chemical composition formed as a separate package;

(v) an agricultural chemical formulation comprising a separate package of a composition comprising at least one kind of compound (A) represented by the general formula (I) and a chelating agent (D), a separate package of at least one kind of surfactant (C) other than the compound (A), and an agricultural chemical composition formed as a separate package; and (vi) an agricultural chemical formulation comprising at least one kind of compound (A) represented by the general formula (I), a separate package of a composition comprising at least one kind of surfactant (C) other than the compound (A) and a chelating agent (D), and an agricultural chemical composition formed as a separate package. This agricultural chemical composition formed as a separate package means a composition in a form such as an emulsifiable concentrate, a wettable powder etc., containing a technical material of agricultural chemical and arbitrary components in an arbitrary ratio, and is different from the agricultural chemical composition comprising the enhancer for agricultural chemicals in the present invention and a technical material of agricultural chemical. The form of each separate package is not limited, and is prepared depending on its intended use and object.

By combination with a technical material of agricultural chemical itself, the compound of the present invention exhibits an excellent effect-enhancing action on agricultural chemicals and is excellent in stability even if the compound is compounded at a high concentration. Although not wanting to be limited by the compound (A) of the present invention is an amine oxide of a specific structure having an amide alkyl group or an oxyalkylene group in the molecule, and is superior to the usual amine oxide in stability when compounded in agricultural chemicals, and increases the permeability and transferability of the agricultural chemicals, resulting in exerting an excellent enhancing action on the effect of the agricultural chemicals. Further, the compound (A) of the present invention also gives a preferable effect such as excellent biodegradation attributable to its structure.

EXAMPLES

Example 1

A mixture containing the compound (A) as the active ingredient in an amount shown in Table 1 and water, and if necessary the surfactant (C) and the chelating agent (D) shown in Table 2, were used to prepare various enhancers for agricultural chemicals (hereinafter, referred to as the active ingredient) shown in Table 2.

TABLE 1

Mixture containing the compound (A) and water

| No. | $R^1$ | A | $R^2$ and $R^3$ | Content of the active ingredient (weight-%) |
|---|---|---|---|---|
| ① | n-$C_{11}H_{23}$ | —CONH$(CH_2)_3$— | $CH_3$ | 40 |
| ② | n-$C_{13}H_{27}$ | —CONH$(CH_2)_3$— | $CH_3$ | 40 |
| ③ | Coconut oil fatty acid residue[1] | —CONH$(CH_2)_2$— | $CH_3$ | 40 |
| ④ | Tallow fatty acid residue[2] | —CONH$(CH_2)_3$— | $C_2H_5$ | 40 |
| ⑤ | Coconut oil fatty acid residue[1] | —CONH$(CH_2)_3$— | Coconut oil alkyl[4] | 30 |
| ⑥ | n-$C_{17}H_{35}$ | —CONH$(CH_2)_3$— | —$(C_2H_4O)_1$—H | 40 |
| ⑦ | Coconut oil fatty acid residue[1] | —(OC$_2H_4)_{10}$— | —$(C_2H_4O)_1$—H | 40 |
| ⑧ | Coconut oil fatty acid residue[1] | —(OC$_2H_4)_3$— | —$(C_2H_4O)_{10}$—H | 30 |
| ⑨ | $C_{11-15}$ alkyl group[3] | —CONH$(CH_2)_3$— | —$(C_2H_4O)_1$—$(C_3H_7O)_2$—H | 30 |
| ⑩ | n-$C_{13}H_{27}$ | —(OC$_2H_4)_5$— | —$(C_2H_4O)_3$—$(C_3H_7O)_5$—H | 30 |
| ⑪ | n-$C_{12}H_{25}$ | — | $CH_3$ | 40 |

[1] Moiety of coconut oil fatty acid from which COOH was removed.
[2] Moiety of tallow fatty aci from which COOH was removed.
[3] Moiety of $C_{12-16}$ synthetic fatty acid from which COOH was removed.
[4] Moiety of coconut oil alcohol from which COOH was removed.

TABLE 2

| Active Ingredient No. | Compound (A) | Surfactant (C) | Chelating agent (D) | (A)/(C)/(D) ratio by weight | (A)/(D) molar ratio |
|---|---|---|---|---|---|
| 1 | ① | — | — | 100/0/0 | — |
| 2 | ① | POE(20) sorbitan monooleate | — | 80/20/0 | — |
| 3 | ① | — | Potassium oxalate | 90/0/10 | 1/0.53 |
| 4 | ② | — | — | 100/0/0 | — |
| 5 | ② | POE(9) oleyl ether | — | 80/20/0 | — |
| 6 | ② | — | EDTA.4Na | 85/0/15 | 1/0.50 |
| 7 | ③ | — | — | 100/0/0 | — |
| 8 | ③ | Ditrimonolauryl ammonium chloride | — | 80/20/0 | — |
| 9 | ③ | POE(9) lauryl ether | Na gluconate | 70/20/10 | 1/0.54 |
| 10 | ④ | — | — | 100/0/0 | — |
| 11 | ④ | POE(7) secondary alkyl ($C_{12-13}$)ether | — | 70/30/0 | — |
| 12 | ④ | — | Cysteine | 95/0/5 | 1/0.47 |

TABLE 2-continued

| Active Ingredient No. | Compound (A) | Surfactant (C) | Chelating agent (D) | (A)/(C)/(D) ratio by weight | (A)/(D) molar ratio |
|---|---|---|---|---|---|
| 13 | ⑤ | — | — | 100/0/0 | — |
| 14 | ⑤ | POE(20) lauryl ether Na sulfate | — | 70/30/0 | — |
| 15 | ⑤ | — | NTA | 80/0/20 | 1/2.24 |
| 16 | ⑥ | — | — | 100/0/0 | — |
| 17 | ⑥ | POE(10) oleate | — | 70/30/0 | — |
| 18 | ⑥ | — | Potassium oxalate | 90/0/10 | 1/0.72 |
| 19 | ⑦ | — | — | 100/0/0 | — |
| 20 | ⑦ | POE(30) sorbitan tetraoleate | — | 80/20/0 | — |
| 21 | ⑦ | POE(9) oleyl ether | — | 80/20/0 | — |
| 22 | ⑧ | — | — | 100/0/0 | — |
| 23 | ⑧ | POE(3)POP(2)POE(3) lauryl ether | — | 80/20/0 | — |
| 24 | ⑧ | — | Na peptonate | 95/0/5 | 1/0.89 |
| 25 | ⑨ | — | — | 100/0/0 | — |
| 26 | ⑨ | POE(20) lauryl ether | — | 60/40/0 | — |
| 27 | ⑨ | — | Na gluconate | 95/0/5 | 1/0.45 |
| 28 | ⑩ | — | — | 100/0/0 | — |
| 29 | ⑩ | POE(18) glycerin palm fatty ester | — | 50/50/0 | — |
| 30 | ⑩ | — | EDTA.4Na | 90/0/10 | 1/1.45 |
| 31 | — | POE(10) nonylphenyl ether | — | 0/100/0 | — |
| 32 | — | POE(20) lauryl ether | — | 0/100/0 | — |
| 33 | ⑪ | — | — | 100/0/0 | — |

In Table 2, POE is an abbreviation of polyoxyethylene, POP is an abbreviation of polyoxypropylene, and the number in parentheses is the average number of molecules added.

The active ingredient was dissolved in deionized water to prepare a dilution at 600 ppm. Commercial herbicides, Touchdown liquid formulation (38 weight-% glyphosate trimesium as the active ingredient) and Roundup liquid formulation (41.0 weight-% glyphosate isopropylamine as the active ingredient), were diluted with the above 600 ppm dilution such that the active ingredient in the Touchdown liquid formulation was diluted to a concentration of 3800 ppm and the active ingredient in the Roundup liquid formulation to a concentration of 1500 ppm, to produce agricultural chemical compositions in triplicate for each active ingredient.

In a test at a greenhouse, seeds of crabgrass were sowed and germinated in pots with an inner diameter of 12 cm containing soil wherein fertile soil collected from a paddy, river sand, and commercial leaf mold had been mixed in the ratio of 7:2:1 (ratio by weight). To improve the uniformity of seedlings in the pots, a pot with abnormal growth was discarded. Pots wherein the crabgrass had grown to reach about 35 cm in height were used in the test. The agricultural chemical compositions were sprayed uniformly on the whole of the plants in an amount of 5 L/are (5 L/100 m$^2$) for both of Touchdown liquid formulation and Roundup liquid formulation by using a spray gun (RG type, manufactured by Iwata Tosohki Kogyo Co., Ltd.), to evaluate their herbicidal effect.

To evaluate the herbicidal effect, the above-ground fresh weight (%) was measured on the fourteenth day after spraying and expressed as a ratio (herbicidal ratio) relative to the weight of the untreated plants above-ground (see the equation shown below). The herbicidal ratio of each agricultural chemical composition is shown in Table 3.

$$\text{Herbicidal ratio (\%)} = \frac{\text{above-ground fresh weight (g) of an untreated group} - \text{above-ground fresh weight (g) of a test group}}{\text{Above-ground fresh weight (g) of an untreated group}}$$

TABLE 3

|  | Active Ingredient No. | Herbicidal ratio (%) Roundup liquid formulation | Touchdown liquid formulation |
|---|---|---|---|
| Product of the invention | 1 | 90.5 | 92.2 |
|  | 2 | 97.6 | 95.5 |
|  | 3 | 96.1 | 93.8 |
|  | 4 | 93.8 | 92.4 |
|  | 5 | 94.8 | 95.2 |
|  | 6 | 95.5 | 96.8 |
|  | 7 | 92.8 | 92.7 |
|  | 8 | 98.4 | 92.5 |
|  | 9 | 96.2 | 91.1 |
|  | 10 | 93.2 | 92.2 |
|  | 11 | 96.6 | 94.1 |
|  | 12 | 92.2 | 97.2 |
|  | 13 | 94.6 | 94.1 |
|  | 14 | 92.8 | 93.2 |
|  | 15 | 93.3 | 98.0 |
|  | 16 | 89.9 | 96.4 |
|  | 17 | 94.8 | 93.5 |
|  | 18 | 93.1 | 94.2 |
|  | 19 | 92.2 | 90.5 |
|  | 20 | 94.6 | 92.4 |
|  | 21 | 92.0 | 92.2 |
|  | 22 | 90.8 | 90.4 |
|  | 23 | 94.8 | 96.4 |
|  | 24 | 96.1 | 95.3 |
|  | 25 | 91.1 | 93.1 |
|  | 26 | 93.8 | 95.8 |
|  | 27 | 94.4 | 94.9 |
|  | 28 | 96.8 | 92.7 |
|  | 29 | 95.8 | 94.2 |
|  | 30 | 94.8 | 92.2 |

TABLE 3-continued

|  | Active Ingredient No. | Herbicidal ratio (%) | |
|---|---|---|---|
|  |  | Roundup liquid formulation | Touchdown liquid formulation |
| Comparative product | 31 | 72.6 | 75.4 |
|  | 32 | 80.1 | 82.4 |
|  | 33 | 85.9 | 90.4 |
| Added none |  | 61.5 | 60.2 |
| Untreated group |  | 0.0 | 0.0 |

* During the test, there was no problem in the state of plant growth in the untreated group.

Example 2

Thirty female Kanzawa spider mites (*Tetranychus kanzawai* Kishida) were planted onto a leaf disk of a kidney bean by 3 reciprocations, and then incubated for 24 hours at 25° C. Then, the whole of the leaf disk was dipped in a test solution for 5 seconds, then removed from the test solution, left at 25° C. for 48 hours and examined to determine the miticidal ratio relative to that of the untreated group (see the equation below) As the miticides, dilutions prepared by diluting a Nissolan wettable powder (10 weight-% hexythiazox as the active ingredient) and an Osadan wettable powder 25 (25 weight-% phenbutatinoxide as the active ingredient) 3000-fold were used, and the same enhancer for agricultural chemicals as in Example 1 was used. The enhancer for agricultural chemicals was diluted to give a dilution containing the active ingredient at a concentration of 0.1% by weight. For the untreated group, the same procedure as above was carried out except that the enhancer for agricultural chemicals was not used. The results are shown in Table 4.

$$\text{Miticidal ratio (\%)} = \frac{\text{the number of living mites in the untreated group} - \text{the number of living mites in the test group}}{\text{the number of living mites in the untreated group}}$$

TABLE 4

|  | Active Ingredient No. | Miticidal ratio (%) | |
|---|---|---|---|
|  |  | Nissorun wettable powder | Osadan 25 wettable powder |
| Product of the invention | 1 | 87.4 | 89.4 |
|  | 2 | 89.5 | 94.0 |
|  | 3 | 90.6 | 95.2 |
|  | 4 | 92.8 | 93.9 |
|  | 5 | 100.0 | 96.3 |
|  | 6 | 93.9 | 93.8 |
|  | 7 | 93.8 | 91.9 |
|  | 8 | 95.1 | 92.9 |
|  | 9 | 95.0 | 91.7 |
|  | 10 | 95.3 | 91.6 |
|  | 11 | 94.1 | 94.0 |
|  | 12 | 94.2 | 95.2 |
|  | 13 | 92.9 | 90.7 |
|  | 14 | 96.3 | 91.8 |
|  | 15 | 91.9 | 92.7 |
|  | 16 | 95.3 | 91.0 |
|  | 17 | 94.3 | 95.2 |
|  | 18 | 93.3 | 93.8 |
|  | 19 | 98.5 | 91.9 |
|  | 20 | 92.8 | 95.2 |
|  | 21 | 93.9 | 98.8 |
|  | 22 | 88.8 | 94.0 |

TABLE 4-continued

|  | Active Ingredient No. | Miticidal ratio (%) | |
|---|---|---|---|
|  |  | Nissorun wettable powder | Osadan 25 wettable powder |
|  | 23 | 93.0 | 96.3 |
|  | 24 | 96.4 | 96.5 |
|  | 25 | 91.1 | 92.0 |
|  | 26 | 94.1 | 95.4 |
|  | 27 | 95.2 | 97.6 |
|  | 28 | 96.4 | 92.9 |
|  | 29 | 96.3 | 94.1 |
|  | 30 | 94.3 | 95.3 |
| Comparative product | 31 | 63.1 | 66.7 |
|  | 32 | 64.7 | 65.1 |
|  | 33 | 83.7 | 86.4 |
| Added none |  | 51.7 | 55.8 |
| Untreated group |  | 0.0 | 0.0 |

Example 3

Three groups consisting of the third instar of rice planthopper larvae, 10 insects/group, were raised, and the effect of an insecticide thereon was evaluated by a dipping method. The insecticidal ratio was determined in the same manner as for the miticidal ratio. Dilutions prepared by diluting commercial insecticides, a Sumithion emulsifiable concentrate (50 weight-% MEP as the active ingredient) and a Trebon emulsifiable concentrate (20 weight-% ethofenproxas the active ingredient) 3000-fold were used, and the same enhancer for agricultural chemicals as in Example 1 was used after diluting at a concentration of 0.1% by weight in the dilution of the insecticide.

TABLE 5

|  | Active Ingredient No. | Insecticidal ratio (%) | |
|---|---|---|---|
|  |  | Sumithion emulsifiable concentrate | Trebon emulsifiable concentrate |
| Product of the invention | 1 | 83.3 | 83.3 |
|  | 2 | 80.0 | 86.7 |
|  | 3 | 83.3 | 86.7 |
|  | 4 | 90.0 | 83.3 |
|  | 5 | 93.3 | 90.0 |
|  | 6 | 96.7 | 90.0 |
|  | 7 | 93.3 | 83.3 |
|  | 8 | 90.0 | 93.3 |
|  | 9 | 93.3 | 93.3 |
|  | 10 | 86.7 | 86.7 |
|  | 11 | 83.3 | 90.0 |
|  | 12 | 83.3 | 90.0 |
|  | 13 | 80.0 | 76.7 |
|  | 14 | 86.7 | 86.7 |
|  | 15 | 90.0 | 90.0 |
|  | 16 | 76.7 | 83.3 |
|  | 17 | 80.0 | 90.0 |
|  | 18 | 80.0 | 86.7 |
|  | 19 | 86.7 | 80.0 |
|  | 20 | 90.0 | 80.0 |
|  | 21 | 76.7 | 80.0 |
|  | 22 | 83.3 | 90.0 |
|  | 23 | 86.7 | 93.3 |
|  | 24 | 90.0 | 96.7 |
|  | 25 | 83.3 | 80.0 |
|  | 26 | 83.7 | 83.3 |
|  | 27 | 83.7 | 83.3 |
|  | 28 | 80.0 | 86.7 |
|  | 29 | 76.7 | 86.7 |
|  | 30 | 86.7 | 86.7 |

TABLE 5-continued

|  | Active Ingredient No. | Insecticidal ratio (%) | |
|---|---|---|---|
| | | Sumithion emulsifiable concentrate | Trebon emulsifiable concentrate |
| Comparative product | 31 | 60.9 | 56.7 |
| | 32 | 58.6 | 60.0 |
| | 33 | 80.0 | 76.9 |
| Added none | | 46.7 | 43.3 |
| Untreated group | | 0.0 | 0.0 |

Example 4

A spore suspension ($10^7$/ml) of cucumber gray mold (*Botrytis cinerea*) acquiring the resistance against fungicides was applied to young cucumber seedlings at the trifoliate stage in a dose of 10 ml per pot and the resulting seedlings were allowed to stand at 25° C. under a relative humidity of 90% for one day.

A commercial Benlate wettable powder (50 weight-% benomyl as the active ingredient) as an insecticide was diluted 2000-fold with a 2500-fold dilution of the active ingredient used in Example 1 and then sprayed in an amount of 5 ml per pot. Thereafter, the sample was left at 25° C. under 85% relative humidity, and the number of disease spots was counted, and the control value relative to the untreated group was calculated according to the following equation. The results are shown in Table 6.

$$\text{Preventive value} = \left[1 - \frac{\text{The number of lesions of a test group}}{\text{The number of lesions of an untreated group}}\right] \times 100$$

TABLE 6

|  | Active Ingredient No. | Preventive value Benlate wettable powder |
|---|---|---|
| Product of the invention | 1 | 86.3 |
| | 2 | 83.0 |
| | 3 | 83.6 |
| | 4 | 82.1 |
| | 5 | 84.5 |
| | 6 | 86.7 |
| | 7 | 95.2 |
| | 8 | 90.0 |
| | 9 | 92.3 |
| | 10 | 87.6 |
| | 11 | 85.4 |
| | 12 | 86.6 |
| | 13 | 81.2 |
| | 14 | 87.6 |
| | 15 | 80.9 |
| | 16 | 87.6 |
| | 17 | 90.3 |
| | 18 | 90.3 |
| | 19 | 86.7 |
| | 20 | 88.9 |
| | 21 | 86.7 |
| | 22 | 91.5 |
| | 23 | 95.5 |
| | 24 | 90.5 |
| | 25 | 88.9 |
| | 26 | 87.5 |
| | 27 | 88.5 |
| | 28 | 91.5 |

TABLE 6-continued

|  | Active Ingredient No. | Preventive value Benlate wettable powder |
|---|---|---|
| | 29 | 93.8 |
| | 30 | 96.6 |
| Comparative product | 31 | 63.9 |
| | 32 | 65.7 |
| | 33 | 79.1 |
| Added none | | 53.4 |
| Untreated group | | 0.0 |

In Examples 1 to 4, the effects of the enhancers for agricultural chemicals according to this invention are compared with a usual amine oxide i.e. lauryl dimethylamine oxide as an enhancer for agricultural chemicals or with comparative products not using the enhancer compound of this invention. As is evident from Tables 3 to 6, it is recognized that the products of this invention exhibit a higher effect-enhancing action on agricultural chemicals than that of the comparative products, and exert a significant effect particularly on the herbicides or miticides, to enhance the effect of the agricultural chemicals specifically.

As shown in Tables 1 and 2, the products of this invention were obtained at the maximum concentration of 40 weight-%, and even when compounded at such high concentration, the composition was excellent in stability without causing separation of the ingredients.

What is claimed is:

1. An agricultural chemical composition comprising the following components (A) and (B):

(A)

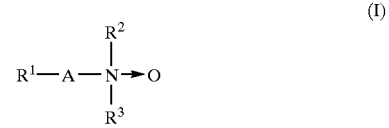

(I)

wherein $R^1$ represents a $C_{6-30}$ linear or branched alkyl group, a $C_{6-30}$ linear or branched alkenyl group, or an alkylphenyl group having a $C_{6-17}$ alkyl group; $R^2$ and $R^3$ each represents —$(A^1O)_m$—H; and A represents —CONH$(CH_2)_n$—;

wherein $A^1$ represents a $C_{2-4}$ alkylene group, the average of m is a number of 1 to 30, and the average of n is a number of 1 to 15, and (B) a technical material of agricultural chemical selected from the group consisting of a herbicide selected from glyphosate and bialaphos.

2. The agricultural chemical composition according to claim 1, which further comprises a surfactant (C) other than (A).

3. The agricultural chemical composition according to claim 1 or 2, which further comprises a chelating agent (D).

4. The agricultural chemical composition according to claim 2, wherein the (A)/(C) ratio is in the range of 1/10 to 50/1 by weight.

5. The agricultural chemical composition according to claim 3, wherein the molar ratio of (D) to (A) is in the range of 0.05 to 15.

6. A method of enhancing the effect of component (B) comprising the steps of (a) mixing component (A) described in claim 1 with component (B) described in claim 1; and (b) applying mixture of said component (A) and said component (B) to weeds.

7. A method of killing a weed comprising the steps of
(a) diluting the composition of claim 1; and
(b) applying said diluted solution to weeds.

8. An agricultural chemical composition comprising the following components (A) and (B):

(A)

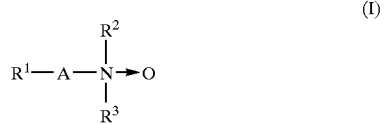

(I)

wherein $R^1$ represents a $C_{6-30}$ linear or branched alkyl group, a $C_{6-30}$ linear or branched alkenyl group, or an alkylphenyl group having a $C_{6-17}$ alkyl group; $R^2$ and $R^3$ each represents a $C_{1-30}$ linear or branched alkyl group, a $C_{1-30}$ linear or branched alkenyl group, or —$(A^1O)_m$—H; A represents —$CONH(CH_2)_n$— or —$(OA^1)_m$—; $A^1$ represents a $C_{2-4}$ alkylene group, the average of m is a number of 1 to 30, and the average of n is a number of 1 to 15, and (B) at least one technical material of an agricultural chemical selected from the group consisting of an insecticide, a fungicide or a bactericide and a miticide.

9. The agricultural chemical composition according to claim 8, which further comprises a surfactant (C) other than (A).

10. The agricultural chemical composition according to claim 8 or 9, which further comprises a chelating agent (D).

11. The agricultural chemical composition according to claim 9, wherein the (A)/(C) ratio is in the range of 1/10 to 50/1 by weight.

12. The agricultural chemical composition according to claim 10, wherein the molar ratio of (D) to (A) is in the range of 0.05 to 15.

13. A method of enhancing the effect of (B) comprising the steps of
(a) mixing component (A) described in claim 8 with component (B) described in claim 9; and
(b) applying the mixture of said component (A) and said component (B) to fungi or bacteria, insects, mites or plants.

14. A method of killing fungi, bacteria, insects or mites comprising the steps of
(a) diluting the composition of claim 8; and
(b) applying said diluted solution to fungi, bacteria, insects, mites or plants.

* * * * *